United States Patent
Jensen et al.

(10) Patent No.: US 12,123,863 B2
(45) Date of Patent: Oct. 22, 2024

(54) PROCESSES AND SYSTEMS FOR DETERMINING IF DOWNHOLE FLUIDS ARE IN EQUILIBRIUM OR NON-EQUILIBRIUM

(71) Applicant: Schlumberger Technology Corporation, Sugar Land, TX (US)

(72) Inventors: Melanie Jensen, Cambridge, MA (US); Lalitha Venkataramanan, Lexington, MA (US); Sandip Bose, Chestnut Hill, MA (US); Peter Tilke, Watertown, MA (US); Oliver C. Mullins, Houston, TX (US); Li Chen, Beijing (CN); Denise E. Freed, Newton Highlands, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 12 days.

(21) Appl. No.: 18/043,616

(22) PCT Filed: Sep. 2, 2021

(86) PCT No.: PCT/US2021/071354
§ 371 (c)(1),
(2) Date: Mar. 1, 2023

(87) PCT Pub. No.: WO2022/051764
PCT Pub. Date: Mar. 10, 2022

(65) Prior Publication Data
US 2023/0349881 A1    Nov. 2, 2023

Related U.S. Application Data

(60) Provisional application No. 63/073,788, filed on Sep. 2, 2020.

(51) Int. Cl.
*G01N 33/28*    (2006.01)
*E21B 49/08*    (2006.01)

(52) U.S. Cl.
CPC ....... *G01N 33/2823* (2013.01); *E21B 49/081* (2013.01)

(58) Field of Classification Search
CPC .... G01N 33/2823; E21B 49/081; E21B 43/00
See application file for complete search history.

(56) References Cited

U.S. PATENT DOCUMENTS 8,825,408 B2    9/2014  Freed et al.
9,074,460 B2    7/2015  Pomerantz
(Continued)

FOREIGN PATENT DOCUMENTS

EP    2286062 A4    5/2017

OTHER PUBLICATIONS

Mullins, O. C. et al., "Downhole Fluid Analysis Coupled with Novel Asphaltene Science for Reservoir Evaluation", 2010, SPWLA 51st Annual Logging Symposium, Society of Petrophysicists and Well-Log Analysts, pp. 1-11.

(Continued)

*Primary Examiner* — Lam S Nguyen
(74) *Attorney, Agent, or Firm* — Jeffrey D. Frantz

(57) ABSTRACT

Processes and systems for determining asphaltene equilibrium between two or more downhole geographic locations are provided. In some embodiments, the process can include measuring one or more fluid properties of a plurality of fluid samples at varying downhole depths to generate a one or more downhole fluid analysis measurement data points; selecting an asphaltene diameter distribution based on prior knowledge; utilizing the asphaltene diameter distribution to fit a first set of one or more equation of state curves to the one or more downhole fluid analysis measurement data points to define a first model of fitted equation of state curves and to determine one or more posterior distributions of asphaltene diameters; and determining if the varying down- (Continued)

hole depths are in an asphaltene equilibrium by determining whether the one or more posterior distributions of asphaltene diameters is consistent with that of asphaltenes in equilibrium.

20 Claims, 6 Drawing Sheets

(56) References Cited

U.S. PATENT DOCUMENTS

| | | |
|---|---|---|
| 2009/0071239 A1 | 3/2009 | Rojas |
| 2013/0151159 A1 | 6/2013 | Pomerantz et al. |
| 2014/0202237 A1 | 7/2014 | Pomerantz |
| 2015/0185360 A1 | 7/2015 | Freed |
| 2016/0252454 A1 | 9/2016 | Zuo |
| 2016/0348480 A1 | 12/2016 | Zuo |
| 2018/0004863 A1 | 1/2018 | Zuo |
| 2018/0223657 A1 | 8/2018 | Zuo |

OTHER PUBLICATIONS

Pfeiffer, T. et al., "Determination of Fluid Composition Equilibrium under Consideration of Asphaltenes—a Substantially Superior Way to Assess Reservoir Connectivity han Formation Pressure Surveys", SPE 145609, 2011 SPE Annual Technical Conference and Exhibition, Society of Petroleum Engineers, pp. 1-12.

Zuo, J. Y. et al., "Advances in the Flory-Huggins-Zuo Equation of State for Asphaltene Gradients and Formation Evaluation", Energy Fuels, 2012, 27(4), pp. 1722-1735.

Chen, L. et al., "A Study of Connectivity and Baffles in a Deepwater Gulf of Mexico Reservoir Linking Downhole Fluid Analysis and Geophysics", SPE 187231, 2017 SPE Annual Technical Conference and Exhibition, Society of Petroleum Engineers, 19 pages.

Zuo, J. Y. et al., "Diffusion Model Coupled with the Flory-Huggins-Zuo Equation of State and Yen-Mullins Model Accounts for Large Viscosity and Asphaltene Variations in a Reservoir Undergoing Active Biodegradation", Energy Fuels, 2015, 29(3), pp. 1447-1460.

International Search Report and Written Opinion issued in the PCT Application PCT/US2021/071354, dated Dec. 20, 2021 (11 pages).

Mullins, O.C., (2020). Reservoir Fluid Geodynamics and Reservoir Evaluation. Houston, Texas: Schlumberger, p. 243.

International Preliminary Report on Patentability issued in the PCT Application PCT/US2021/071354, dated Mar. 16, 2023, 7 pages.

Exam Report under Section 18(3) issued in the United Kingdom Patent No. GB2302456.5 dated Mar. 22, 2024, 6 pages.

PROCESSES AND SYSTEMS FOR DETERMINING IF DOWNHOLE FLUIDS ARE IN EQUILIBRIUM OR NON-EQUILIBRIUM

CROSS REFERENCE TO RELATED APPLICATION(S)

This application is a National Stage Entry of International Application No. PCT/US2021/071354, filed on Sep. 2, 2021, which claims priority to U.S. Provisional Patent Application No. 63/073,788, filed on Sep. 2, 2020, which is incorporated by reference herein.

FIELD

This disclosure relates to downhole fluid analysis. More particularly, this disclosure relates to processes for determining if downhole fluids are in equilibrium or non-equilibrium between two or more downhole locations.

BACKGROUND

Reservoir crude oils consist of dissolved gases, liquids, and dissolved solids. Asphaltenes are the dissolved solids components of crude oils. Asphaltene gradients can be an indicator of reservoir connectivity or indicate that geologic processes may raise reservoir concerns such as connectivity, baffling, tar mat and heavy oil formation, viscosity gradients, asphaltene onset pressure, bitumen deposition, tar mat formation, gas-to-oil ratio (GOR) gradients, biodegradation, and flow assurance. Currently, the modeling of asphaltene gradients is done through the manual evaluation of a downhole fluid analysis (DFA) optical density gradient, as optical density is considered proportional to asphaltene content. The optical density measurements are fit to an equation of state (EOS). One method of modeling asphaltene gradients is based on the Flory-Huggins-Zuo equation of state (the "FHZ EOS"), a thermodynamic model for the asphaltene gradients in a reservoir due to the three forces: gravity, solubility, and entropy. Specifically, the FHZ EOS is given by $$\frac{\phi_a(h_1)}{\phi_a(h_{ref})} = \frac{OD(h_1)}{OD(h_{ref})} \quad \text{(Eq. 1)}$$
$$= \exp(Grav(h_1, h_{ref}) + Sol(h_1, h_{ref}) + Entro(h_1, h_{ref}))$$

where the gravity, solubility, and entropy terms are $$Grav(h_1, h_{ref}) = \frac{v_a g(\rho - \rho_a)(h_1 - h_{ref})}{RT}$$
$$Sol(h_1, h_{ref}) = \frac{v_a}{RT}\left[(\delta_a - \delta)^2_{h_1} - (\delta_a - \delta)^2_{h_{ref}}\right]$$
$$Entro = \left[\left(\frac{v_a}{v}\right)_{h_{ref}} - \left(\frac{v_a}{v}\right)_{h_1}\right]$$

respectively. See Zuo, J. Y., Mullins, O. C., Freed, D., Elshahawi, H., Dong, C., & Seifert, D. J. (2013). Advances in the Flory-Huggins-Zuo equation of state for asphaltene gradients and formation evaluation. Energy & Fuels, 27(4), 1722-1735. The variables $\phi$, OD, R, v, $\delta$, T, g, $\rho$, and h are the volume fraction, optical density, universal gas constant, molar volume, Hildebrand solubility parameter, temperature, earth's gravitational acceleration, density, and depth, respectively. The subscript a denotes the properties of the asphaltenes, whereas the subscripts $h_1$ and $h_{ref}$ denote the properties at depths $h_1$ and $h_{ref}$ respectively. The pair ($h_{ref}$, $OD_{ref}$) is called the reference point as asphaltene gradient is exactly equal to one when $h_1 = h_{ref}$.

There are several known implementations of this process. The first is solving the FHZ EOS exactly. (Suitable processes can include the processes disclosed in U.S. Pat. No. 8,825,408). Other methods solve approximations to the FHZ EOS. (Suitable processes can include the processes disclosed in U.S. Pat. No. 9,074,460). Regardless of the implementation, the number of distinct FHZ EOS curves and the tunable parameter of the given FHZ EOS equation are manually selected. When using the proxies to the FHZ EOS parameter, the reference point and asphaltene diameter comprise the tunable parameters. Selected asphaltene diameters agreeing with the Yen-Mullins model provide evidence for asphaltene equilibrium. These known methods require significant manual resources.

There is a need therefore for more efficient, automated or semi-automated processes or systems that can determine downhole asphaltene equilibrium or disequilibrium.

SUMMARY

Processes and systems for determining asphaltene equilibrium between two or more downhole geographic locations are provided. In some embodiments, the process can include measuring one or more fluid properties of a plurality of fluid samples at varying downhole depths to generate a one or more downhole fluid analysis measurement data points. The process can further include selecting an asphaltene diameter distribution based on prior knowledge. The process can further include utilizing the asphaltene diameter distribution to fit a first set of one or more equation of state curves to the one or more downhole fluid analysis measurement data points to define a first model of fitted equation of state curve sand to determine one or more posterior distributions of asphaltene diameters. The process can further include determining if the varying downhole depths are in an asphaltene equilibrium by determining whether the one or more posterior distributions of asphaltene diameters is consistent with that of asphaltenes in equilibrium.

In some embodiments, a process for determining asphaltene equilibrium between two or more downhole geographic locations can include measuring one or more fluid properties of a plurality of fluid samples at varying downhole depths to generate a plurality of fluid property measurements. The process can further include correlating the plurality of fluid property measurements and any associated fluid sample measurement uncertainties for each measurement to the downhole depth at which each fluid property was measured to define a one or more downhole fluid analysis measurement data points and related measurement uncertainties associated with a plurality of downhole geographic locations. The process can further include selecting an asphaltene diameter distribution based on prior knowledge of a downhole geographic region. The process can further include utilizing the asphaltene diameter distribution to fit a first set of one or more equation of state curves to the one or more downhole fluid analysis measurement data points and related measurement uncertainties to define a first model and generate one or more posterior distributions of asphaltene diameters and utilizing the asphaltene diameter distribution to fit a second set of one or more equation of state curves to the one or more downhole fluid analysis measurement data points and related measurement uncertainties to define a second model and generate one or more posterior distributions of asphaltene diameters. The process can further include ranking the first and second models by fitted equation of state curves to the one or more downhole fluid analysis measurement data points and related measurement uncertainties to create a top model. The process can further include determining from the top model one or more inferred distributions of fluid properties for the plurality of downhole geographic locations. The process can further include determining if the plurality of downhole geographic locations is in an asphaltene equilibrium by determining whether the one or more inferred distributions of fluid properties are that expected of fluid properties for a particular hydrocarbon type.

BRIEF DESCRIPTION OF DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

Figure 1:
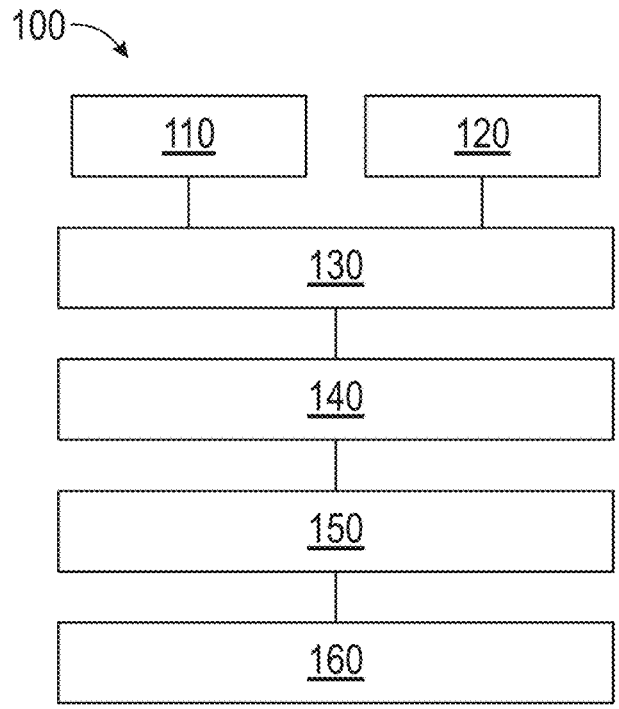
FIG. 1 depicts an illustrative flow diagram for determining asphaltene equilibrium between two or more downhole geographic locations, according to one or more embodiments described.

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements This subject disclosure presents processes and systems that can determine whether there is asphaltene equilibrium between two or more downhole geographic locations. FIG. 1 depicts an illustrative process diagram 100 for determining asphaltene equilibrium between two or more downhole geographic locations, according to one or more embodiments described. In one or more embodiments, the processes and systems can utilize domain knowledge, geological knowledge including zone information, and/or likelihood of presence of different asphaltene types as inputs 110 and downhole fluid analysis (DFA) measurements as inputs 120. For example, the processes and systems can measure one or more fluid properties of a plurality of fluid samples at varying downhole depths to generate a plurality of fluid property measurements. In one embodiment, the plurality of fluid samples can be at least 1, 2, 3, 5, 10, 15, 20, 25, 30, or more fluid samples. The process and system can correlate the plurality of fluid property measurements and any associated fluid sample measurement uncertainties for each measurement, or other errors, to the downhole depth at which each fluid property was measured to define a one or more downhole fluid analysis measurement data points. The one or more measurement uncertainties in the one or more measured fluid properties can include both an inherent stochasticity of the fluids as well as any uncertainty in the measurements. In other embodiments, the one or more downhole fluid analysis measurement data points have related measurement uncertainties and/or are associated with a plurality of downhole geographic locations. In some embodiments, the measured fluid properties can include one or more of optical density data, temperature, pressure, asphaltene concentration, fluid density, fluid viscosity, retrograde dew formation, asphaltene precipitation, or gas evolution. The processes and systems can select an asphaltene diameter distribution 130 based on the domain knowledge, the geological knowledge including zone information, and/or the likelihood of presence of different asphaltene types as inputs 110 and downhole fluid analysis (DFA) measurements as inputs 120. In other embodiments, the asphaltene diameter distribution 130 can include related uncertainties. The processes and systems can perform a model search 140 by generating one or more models of the one or more downhole fluid analysis measurement data points by utilizing the asphaltene diameter distribution to fit a set of one or more equation of state curves to the one or more downhole fluid analysis measurement data points to define a model and determine one or more posterior distributions of asphaltene diameters equation of state curves. In the same fashion, two or more models can be generated along with the one or more posterior distributions of asphaltene diameters. The equations of state can be the same or different equations of state within a model or between models. In other embodiments, the processes and systems can perform a model search 140 by generating two or more models of the one or more downhole fluid analysis measurement data points by utilizing the asphaltene diameter distribution to fit a first set of one or more equation of state curves to the one or more downhole fluid analysis measurement data points and related measurement uncertainties to define a first model and generate one or more posterior distributions of asphaltene and utilizing the asphaltene diameter distribution to fit a second set of one or more equation of state curves to the one or more downhole fluid analysis measurement data points and related measurement uncertainties to define a second model and generate one or more posterior distributions of asphaltene diameters. In the same fashion, a third or more model of fitted equation of state curves can be generated. The first and second, optionally the third, and optionally any subsequent equations of state can be the same or different equations of state within a model or between models.

The processes and systems can score or rank 150 the one or more models to create a top model. In other embodiments, the processes and systems can rank 150 the plurality of models by fitted equation of state curves to the one or more downhole fluid analysis measurement data points and related measurement uncertainties to create a top model and determine from the top model one or more inferred distributions of fluid properties for the plurality of downhole geographic locations. The processes and systems can determine if the plurality of downhole geographic locations is in an asphaltene equilibrium by determining whether the one or more inferred distributions of asphaltene diameter is consistent with that of asphaltenes in equilibrium 160. In other embodiments, the processes and systems can determine if the plurality of downhole geographic locations is in an asphaltene equilibrium by determining whether the one or more inferred distributions of fluid properties are that expected of fluid properties for a particular hydrocarbon type 160. The processes and systems can also determine if the two or more downhole geographic locations belong to the same flow unit, where downhole liquid or gaseous hydrocarbons flow together. Each downhole geographic location can be a function of a borehole depth or can be identified by other geographic location data. For example, the geographic location data can include global positioning system coordinates or other positioning coordinate information.

In some embodiments, the Flory-Huggins-Zuo equation of state as referenced herein by Equation 1 above, can be used to create curves to fit at least two or more DFA measurement data points described above. Other equations of state that can be parameterized using the asphaltene diameter can also be used. For example, any modification of the Flory-Huggins-Zuo equation of state and Peng-Robinson EOS (1976) can also be used.

In one or more embodiments, one or more new downhole geographic location depths can be discriminated between one or more models and one or more new or additional downhole geographic locations can be selected for additional fluid property sampling or other measurements. Further, in addition to reservoir connectivity, three-dimensional geometric assessment for the downhole conditions can be further refined giving insight into the underlying reservoir fluid geodynamics (RFG) processes.

The processes and systems are herein referred collectively as a reservoir fluid geodynamics profiler or the "RFG Profiler." The processes and systems can model asphaltene gradients and perform a model search, including model order through testing over possible reservoir realizations that honors the measured data and prior knowledge of the reservoir. In some embodiments, the prior knowledge can include information known about one or more downhole conditions or parameters. For example, the downhole knowledge can include known geological layers, faults, fluid property measurements, downhole liquid or gaseous hydrocarbon flow, or any combinate thereof.

In one or more embodiments, the processes and systems can provide an explanation of the state of asphaltene equilibrium. Downhole fluid analysis (DFA) measurements can be utilized to determine asphaltene equilibrium, along with the likelihood of the presence of different asphaltene types, and prior domain knowledge of the reservoir, such as geological layers, faults, and/or downhole flow. Applications of these processes and systems can include selecting one or more downhole locations for additional downhole fluid sampling based on the asphaltene equilibrium determination, through comparison of multiple models consistent with the DFA data. The processes and systems can also provide more insight for interpreting both the three-dimensional geometry and connectivity of the reservoir and the fluids and can give insight into the underlying RFG processes. For example, the processes and systems can output the top model onto a graphical display and the data fits on the one or more equation of state curves can be visually assessed to determine if the plurality of downhole geographic locations belong to the same flow unit. For simplicity, for the remainder of this description, embodiments will be described with reference to asphaltene diameter and optical density as example, non-limiting properties utilized for determining downhole conditions and the FHZ EOS will be used.

Model for the Optical Density Data

The processes and systems can utilize prior domain knowledge about the solubility gradient within the reservoir to describe the optical density. If the gravity term in Eq. 1 is known to mainly contribute to the asphaltene gradient, the process assumes the gravity only FHZ, whereas when the solubility term is significant, the process assumes the Fast FHZ. The process captures uncertainty in the optical density by modelling the optical density measured at depth $h_n$ as a random variable, with mean given by one of the two FHZ proxies and known variance:

$$\mathbb{E}(OD_n) = OD_{ref}\exp(d^3 f(h_n, h_{ref})), \mathbb{V}\text{ar}(OD_n) = \sigma_n^2 \quad (\text{Eq 2})$$

where $$f(h_n, h_{ref}) = \begin{cases} Grav(h_n, h_{ref})/d^3 & \text{for gravity only } FHZ \\ Grav(h_n, h_{ref})/d^3 + \overline{\xi_{\text{res}}}(h_n, h_{ref})/d^3 + \\ \overline{\xi_{\text{restres}}}(h_n, h_{ref})/d^3 & \text{for Fast } FHZ \end{cases}$$

Due to the relationship between the reference optical density, $OD_{ref}$, and reference depth, $h_{ref}$, the reference depth is fixed to depth comparable to the depths at which downhole fluid samples are measured, leaving the asphaltene diameter and reference optical density as unknown parameters to be inferred along with their distribution. In one or more embodiments, the reference optical density and reference height can be measured and fixed.

When an alternative EOS model is assumed then the mean of the observed optical density should be that predicted by the EOS. If the EOS has tunable parameters other than the reference optical density and the asphaltene diameter, the additional parameters will be simultaneously inferred from a Bayesian approach, as depicted in Eq. 3.

$$p(d, OD_{ref}|OD_{1:N}) \propto p(OD_{1:N}|d, OD_{ref})p(d, OD_{ref}) \quad (\text{Eq 3})$$

where $p(OD_{1:N}|d, OD_{ref})$ is a likelihood function given the model parameter "d" and "$OD_{ref}$" with "$OD_{1:N}$" referring to the N optical density measurement, "d" referring to the asphaltene diameter, and "$OD_{ref}$" referring to the reference optical density, $p(d, OD_{ref})$ is a prior distribution for asphaltene diameter and reference optical density, $\propto$ means proportional to, and $p(d, OD_{ref}|OD_{1:N})$ is a posterior distribution of the asphaltene diameter and the reference optical density. That is, the reference optical density and asphaltene diameter will be assumed to follow a distribution.

Any variance in optical density can be constant or heterogenous for each measurement and can be fixed. One possible estimator of the variance for a specific measured depth is some proportion of the measured optical density's measurement error. Some possible sources of uncertainty or error in the measured optical density can include the DFA tool, depth, and/or contamination of the downhole fluid samples. Uncertainty due to depth can depend on the type of hydrocarbon in the reservoir. Uncertainty due to contamination can be mitigated by utilizing other DFA measurements. In one or more embodiments, the variance in the optical density can be inferred along with the other model parameters.

Prior Distribution for Asphaltene Diameters

In one or more embodiments, the processes and systems can include prior expert knowledge of the reservoir and Yen-Mullins modeled physics for the asphaltene diameter. The Yen-Mullins model can provide asphaltene diameter equilibrium values, namely for light oil, black oil, and heavy oil. The processes and systems can update the prior knowledge with observed optical density data. From the observed optical density data, the posterior distribution of asphaltene diameters can be obtained by using Eq 3. From the distributions, evidence for asphaltene equilibrium for the corresponding asphaltene gradient can be deduced by how well the posterior distribution agrees with the Yen-Mullins model.

Figure 2:
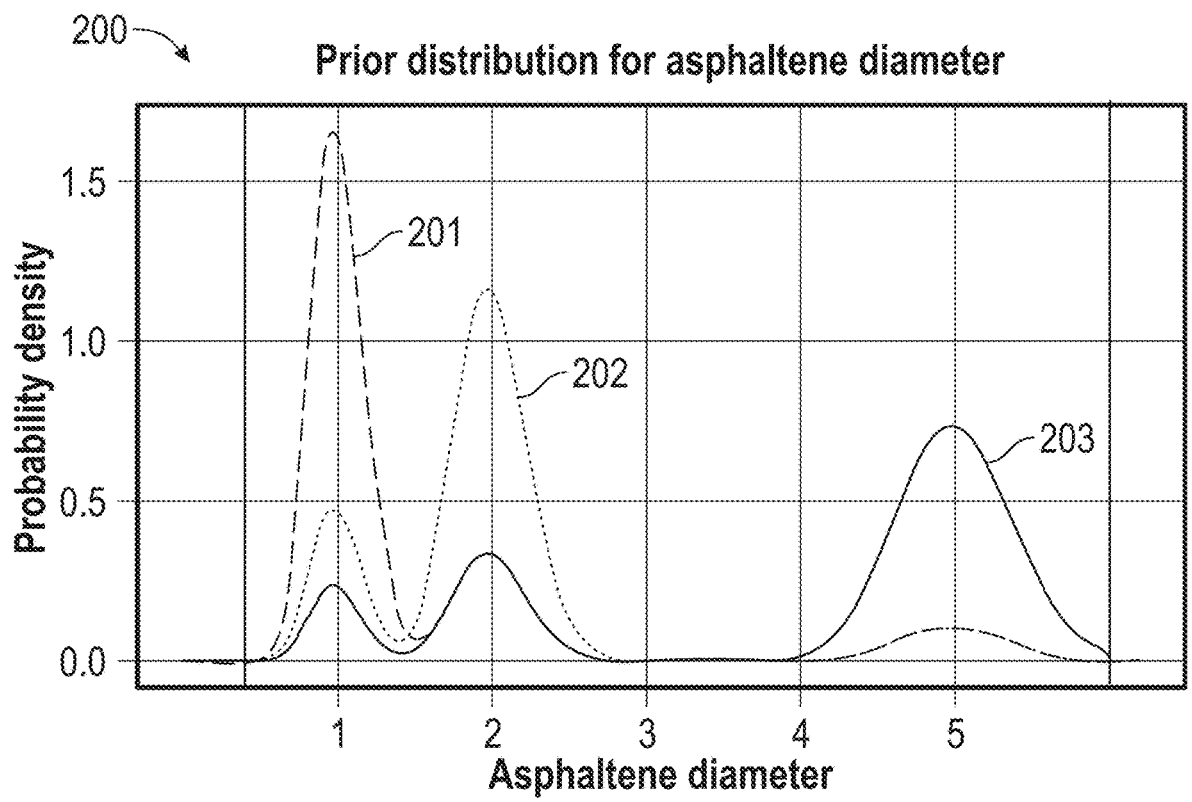
FIG. 2 depicts an illustrative example of a prior distribution for asphaltene diameters for light oil, black oil, and heavy oil, according to one or more embodiments described.

FIG. 2 depicts an illustrative example of a prior distribution 200 for asphaltene diameters for light oil (line 201), black oil (line 202), and heavy oil (line 203), according to one or more embodiments described. As the type of hydrocarbon in the reservoir, light, black, or heavy, dictates the expected asphaltene diameter of asphaltenes in equilibrium as formulated in the Yen-Mullins model, the processes and system can encode the Yen-Mullins model into a probability distribution for the asphaltene diameter. For example, as depicted in FIG. 2, asphaltene diameters for light oil can be about 1.0 nm and made up of molecules, for black oil can be about 2.0 nm and made up of nanoaggregate, and for heavy oil can be about 5.0 nm and made up of a cluster of nanoaggregates. This distribution can be tri-modal and supported on a finite interval. Each mode of the tri-modal distribution can correspond to one of the three equilibrium values, the weight of each mode can depend on prior known hydrocarbon type, and the lower and upper bounds of the distribution set to physically realistic values. Asphaltene diameter values within the lower and upper bound should have non-zero probability. While this prior distribution emphasizes asphaltene diameters corresponding to equilibrium, by having intermediate values with positive probability, non-equilibrium values can still be obtained.

Prior Distribution for Reference Optical Density

The initial knowledge of the type of hydrocarbon can be used to construct a prior probability distribution for the reference optical density. The optical density can be highly variable between reservoirs, so an empirical prior distribution can be used to establish a reservoir specific prior distribution for the reference optical density. The distribution can be a unimodal distribution supported on a finite interval. The mode of the distribution can be located near the value predicted by the measured optical density assuming the equilibrium asphaltene diameter of the initially selected oil, for example light oil, black oil, or heavy oil. The lower and upper bound of the distribution can be obtained by the measured optical density when assuming the lower and upper bound of the asphaltene diameter. The spread of the distribution can be set so the lower and upper bound is no more than a given number of standard deviations away from the mode. For example, the spread can be set such that the maximum standard deviation is no more than about 1.0 standard deviations, 2.0 standard deviations, 3.0 standard deviations, or greater.

Defining Geological Layers

In one or more embodiments, geological layers can be broken into depth zones in which certain reservoir properties within each zone are distinct. For example, a first depth zone may be defined by an upper depth and a lower depth between which there lies a pressure gradient or some other gradient. The selection of one or more depth zones can be based on expert knowledge. Sources of expert knowledge may come from other measured data such as reservoir pressure, other downhole logs, and/or seismic data. For instance, from pressure data, distinct zones can be inferred from regions with different pressure gradients through manual interpretation or using an algorithm.

When geological layers are not known a priori, the measurements are assumed to come from a single layer. When geological layers are known or assumed to be greater than a single layer, for each geological layer the processes and systems can iterate through the process diagram 100, with reference to FIG. 1. Additionally, the process can intake a predefined model prepared by an expert.

Defining One or More Model of Equation of State Curves

In one or more embodiments, models, such as a set of one or more fitted equation of state curves, can include expert-defined assignments of measurements to a specified number of equation of state curves and those defined with a specified number of equation of state curves For the expert-defined models, the one or more downhole fluid analysis measurement data points can be assigned to an equation of state curve and the posterior distribution of the model parameters of the plurality of equation of state curves can be learned through posterior sampling using Eq 3. For models specified by the number of equation of state curves, the description for the optical density measurement given in Eq. 2 can be extended to a mixture model, where each mixture corresponds to an equation of state curve. The posterior distribution of model parameters of the equation of state curves can be obtained through posterior sampling using Eq 3. Post-processing of posterior samples can be performed. "Outlier" downhole fluid analysis measurement data points, those that do not resolve along a given equation of state curve, can be identified and further assessed or ignored within a given model In one or more embodiments, the resultant plurality of model of fitted equation of state curves can be assigned to one of four properties given by the Yen-Mullins model, molecules, nanoaggregates, clusters, and non-equilibrium. Resultant asphaltene diameters corresponding to the same property can be reduced to one asphaltene diameter to reduce over-fitting as the physical implications of the asphaltene diameter are considered.

Uncertainty in the equation of state curves and inferred optical densities can be quantified by the credible intervals, variance, and other measures of spread. Model scoring or ranking can depend on the resulting geological interpretation of the equation of state curves and/or how well the resulting model of equation of state curves describes the data. For the latter, Bayesian model comparison statistic, such as an expected log pointwise predictive density (elpd), can be considered and estimated using the posterior sample.

In another embodiment, sampling of the unknown parameters can be obtained by first assigning measurements to one of the equation of state curves. For example, posterior optimization can be performed to obtain maximum posterior (MAP) estimates for all the parameters. Multiple initializations of the optimization can be performed to ensure convergence to a global maximum. Then the optimization run with the highest posterior density and/or most probable geological interpretation can be used to assign measurements to a given equation of state curve. Assignments can be based on which equation of state curve is the most probable and/or an alternative physical constraint.

Output

For each geological layer, a top few models can be returned based on their ranking. Outputting a graphical representation of all competing models can provide a visual emphasis of regions of uncertainty that can be indicated by one or more of the models. In real-time, the graphical representation can help guide the placement of new downhole geographic locations for additional fluid property or other measurements that can be utilized to discriminate between various models and can thereby add more information helpful to modeling the reservoir and the fluids therein.

For each returned model, evidence for or against asphaltene equilibrium can be deduced by imposing constraints on a posterior estimate of the asphaltene diameters or their posterior distributions. Such constraints should conclude the evidence for equilibrium if the given value or distribution is consistent with an equilibrium value given by the Yen-Mullins model. For example, conclusion on asphaltene equilibrium can be obtained based on whether the posterior distribution overlaps with the expected range of asphaltene diameters for different asphaltene types in equilibrium. For example, those types corresponding to light oil, black oil, and heavy oil.

Treating the equation of state parameters as coming from a distribution rather than a single point value can enable the quantification of uncertainty in the parameter estimate and can add confidence to the determination of asphaltene equilibrium. Uncertainty in predictive quantities, such as optical density and predictive accuracy, can also be captured using the resultant distributions. The uncertainty in inferred and predictive quantities can provide insight into the depths in a reservoir that may need to be further investigated, which can help guide the placement of new downhole measurement locations to reduce uncertainty.

When there is limited knowledge about how many distinct asphaltene gradients exist within a reservoir and which depth are in communication, the processes and systems can perform a model search over the number of EOS curves. All models can be scored and ranked based on their predictive accuracy and/or geological interpretability. The proposed process provides a more efficient approach to exploring different reservoir realizations that honors the theory of asphaltenes and previous knowledge about the reservoir.

When additional data measurements to the DFA data are available, such as pressure data or other well log data, the additional data measurements can be incorporated into the previously developed models to refine them and the results from the proposed process. For example, if pressure data indicates that there are at least three distinct pressure gradients, then a prior distribution can be placed over the number of EOS curves, where for example a model with one or two EOS curves has prior probability of zero, and models with at least three EOS curves have non-zero probability. These additional measurements can be used in the construction of geological layers.

Benefits of the embodiments herein described can include the inclusion of expert knowledge about geological zones and can handle cases of limited knowledge. Benefits can also include allowing experts to compare their interpretation of the reservoir with other hypotheses that best fit the data while honoring other collected log data from the field, for example, wireline log or pressure data, along with the physics of asphaltenes and the geology of the problem.

EXAMPLES

Two real-world examples are presented where DFA data is analyzed using an RFG Profiler. The RFG Profiler is considered successful when one of the top models correctly identifies if the asphaltene is or is not in asphaltene equilibrium and mirrors the FHZ fits obtained by the domain expert. The RFG analysis by the domain expert is taken to be the ground truth. To test the robustness, reservoirs with differing RFG processes (asphaltene equilibrium vs. nonequilibrium) are considered.

Example 1: Tornado Reservoir, Deep Water Gulf of Mexico

The Tornado reservoir is a black oil reservoir in which seismic imaging and wireline data of two wells showed a lower and upper sand in each well but were unable to resolve if the lower and upper sand were in communication. Manual evaluation of the optical density gradient by a domain expert demonstrated that the lower and upper sand were not in communication (disconnected), but each sand was laterally connected across wells. See Chen, L., Forsythe, J. C., Wilkinson, T., Winkelman, B., Meyer, J., Canas, J. A., . . . & Hayden, R. S. (2017, October). A study of connectivity and baffles in a deep-water Gulf of Mexico reservoir linking downhole fluid analysis and geophysics. In SPE Annual Technical Conference and Exhibition. Society of Petroleum Engineers. Additionally, it was found that the asphaltenes in each sand were in equilibrium. Evidence supporting the lower and upper sand being disconnected was concluded from fitting two FHZ curves to the optical density data, one for the upper sand and the other for the lower sand. Moreover, because the two FHZ had asphaltene diameter corresponding to the diameter specified by the Yen-Mullins model for nanoaggregate (d=2 nm), the two FHZ fits provided evidence for lateral connectivity of each sand across wells along with asphaltene equilibrium. This interpretation has been confirmed by two years of production data.

The RFG profiler was run on the DFA data, where the initial oil model was the black oil model and the Fast FHZ was assumed, due to a large measured GOR gradient. The RFG profiler searched for models with up to 5 fitted equation of state curves, along with an expert defined measurement assignments, but did not find more than four distinct fitted equation of state curves.

Figure 3:
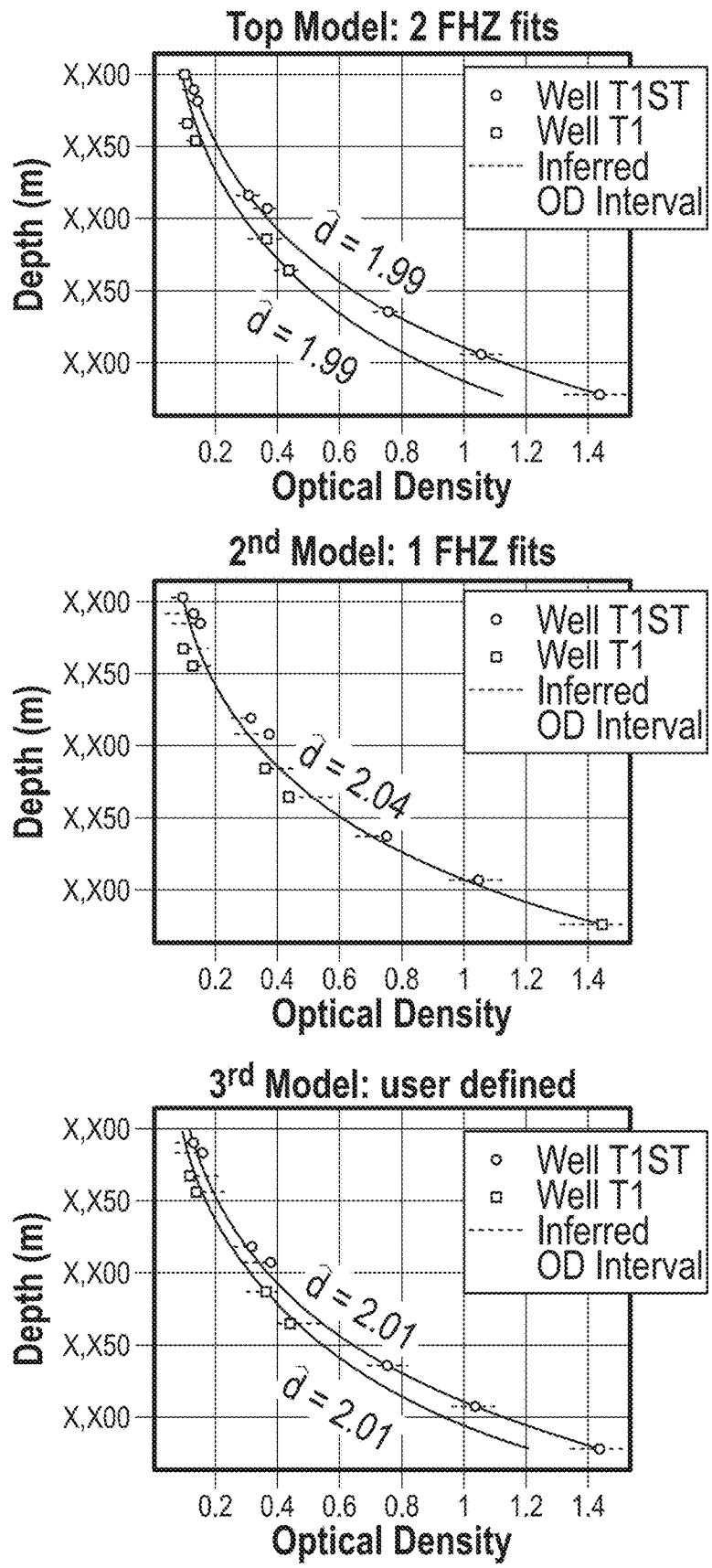
FIG. 3 depicts the top three models obtained by an embodiment herein described for the case study presented in Example 1 described below.

FIG. 3 depicts the top three models 300 obtained by an embodiment herein described for the case study presented in Example 1 described below. Table 1 is an output of relevant data utilized to generate the top models in FIG. 3.

TABLE 1

| Well | Relative Depth (m) | Optical density |
| --- | --- | --- |
| T1ST | 0 | 0.11 |
| T1ST | 9 | 0.14 |
| T1ST | 14 | 0.16 |
| T1ST | 32 | 0.13 |
| T1ST | 45 | 0.15 |
| T1ST | 81 | 0.32 |
| T1ST | 92 | 0.38 |
| T1 | 114 | 0.37 |

TABLE 1-continued

| | | |
|---|---|---|
| T1 | 134 | 0.44 |
| T1 | 161 | 0.75 |
| T1 | 191 | 1.04 |
| T1 | 220 | 1.44 |

| | Most probable values of | |
|---|---|---|
| | Asphaltene diameter | Reference optical density |
| Top Model | | |
| Fit 1 | 1.99 | 0.13 |
| Fit 2 | 1.99 | 0.1 |
| Second Model | | |
| Fit 1 | 2.04 | 0.11 |
| Third Model | | |
| Fit 1 | 2.01 | 0.12 |
| Fit 2 | 2.01 | 0.1 |

The top model and third model were consistent with the expert fitted models, that is the lower and upper sand are not in communication. All top models indicate the asphaltenes were in equilibrium for the black oil model. The assignment of the measurements to the equation of state curves of the first and second model were obtained by posterior optimization, whereas the third was defined by the domain expert.

The uncertainty in the inferred OD measurements is displayed in FIG. 3 by the dashed horizontal lines. All top models provide evidence of asphaltene equilibrium as the estimated asphaltene diameters corresponds to that of nano-aggregates (2 nm). Furthermore, the top model (two fitted equation of state curves) and the third model (expert fitted) are consistent with the model found by the domain expert, that is the lower and upper sand are not in communication. The top and third model only have a slight discrepancy in the inferred FHZ parameters, the main difference in the assignment of the five shallowest optical density measurements. Assigning the three shallowest points to the rightmost FHZ fit (corresponding to the upper sand) and the remaining two to the leftmost FHZ fit (corresponding to the lower sand), was mathematically optimal, whereas assigning the first three to leftmost FHZ fit and last two to the rightmost FHZ fit is consistent with prior geological knowledge.

Example 2: Barmer Basin, India

The Barmer Basin is a black oil reservoir containing five stacked sands with four wells, where biodegradation was a major concern. Manual evaluation of the optical density gradient by a domain expert demonstrated that the oil column was undergoing biodegradation. See Zuo, J. Y., Jackson, R., Agarwal, A., Herold, B., Kumar, S., Santo, I. D., . . . & Mullins, O. C. (2015). Diffusion model coupled with the Flory-Huggins-Zuo equation of state and Yen-Mullins model accounted for large viscosity and asphaltene variations in a reservoir undergoing active biodegradation. Energy & Fuels, 29(3), 1447-1460. The optical density data was fit with a modified FHZ EOS, one that accounts for diffusion, with an asphaltene diameter of 2 nm.

Figure 4:
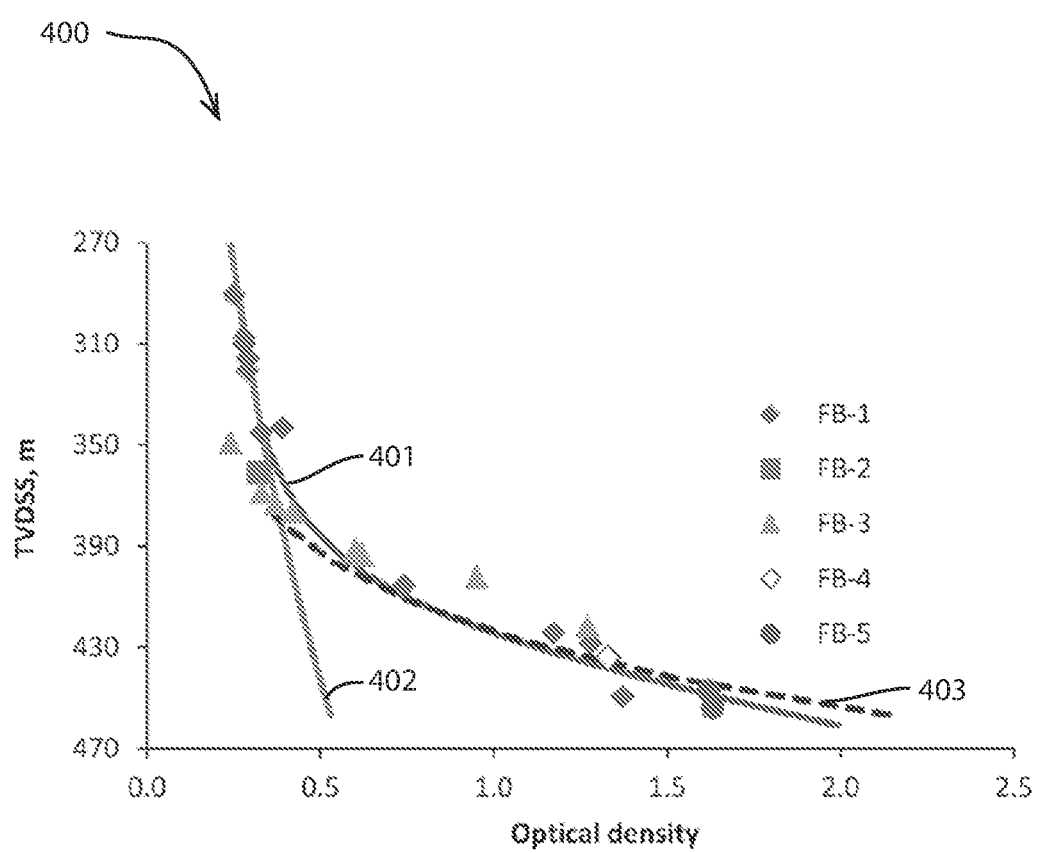
FIG. 4 depicts the FHZ fits presented in Zuo for the reservoir in Example 2.

FIG. 4 depicts the FHZ fits 400 presented in Zuo for the reservoir in Example 2. See Zuo, J. Y., Jackson, R., Agarwal, A., Herold, B., Kumar, S., Santo, I. D., . . . & Mullins, O. C. (2015). Diffusion model coupled with the Flory-Huggins-Zuo equation of state and Yen-Mullins model accounts for large viscosity and asphaltene variations in a reservoir undergoing active biodegradation. Energy & Fuels, 29(3), 1447-1460. The shape of each measurement denotes the sand the measurement came from. Curve 401, curve 402, and curve 403 denote the fitted FHZ EOS with diffusion mode, FHZ EOS only accounting for the gravity term, and the full FHZ EOS, respectively, all with asphaltene diameter of 2 nm.

This model indicated biodegradation and diffusion in the lower portion of the well and equilibrated asphaltenes for black oil in the upper portion of the well as the diffusion gradient did not reach the upper portion. Such model provided evidence for lateral connectivity within a sand, the profile in each sand, and has been confirmed by production data. Unlike Example 1, vertical connectivity of the sands was not concluded from the DFA analysis as often closely stacked sands have the same RFG history and production data has confirmed the sands are vertically disconnected.

The RFG Profiler was run on the DFA data, where the initial oil model was the black oil model and the gravity only model was assumed. While the proposed process did not consider the modified FHZ EOS fit by the domain expert, for all three top models, it provided consistent results. The models were ranked based on posterior predictive accuracy. In all three top models, three curves were found: one corresponding to asphaltene equilibrium for black oil in the upper portion of the well, one not in equilibrium describing the lower portion of the well, and the third FHZ fit picking up points that are far from the other two lines, potentially measurements with large error.

Figure 5:
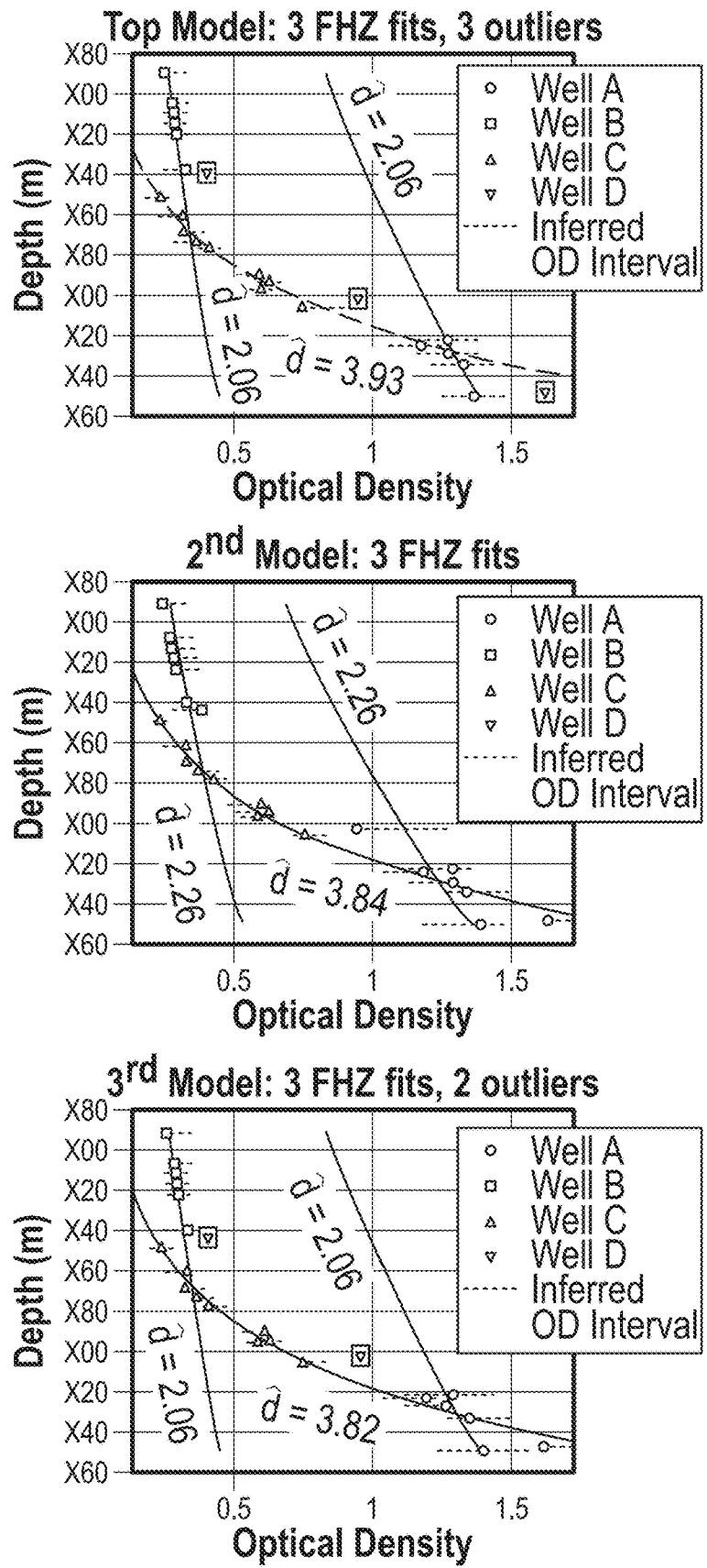
FIG. 5 depicts the top three models obtained by an embodiment herein described for the case study presented in Example 2 described below.

FIG. 5 depicts the top three models obtained by the process for the case study presented in Example 2 described below. Table 2 is an output of the relevant data utilized to generate the top models in FIG. 5.

TABLE 2

| Well | Relative depth (m) | Optical density |
|---|---|---|
| Well A | 290 | 0.25 |
| Well B | 307 | 0.28 |
| Well A | 310 | 0.28 |
| Well A | 316 | 0.29 |
| Well C | 321 | 0.3 |
| Well A | 339 | 0.33 |
| Well C | 343 | 0.39 |
| Well B | 349 | 0.23 |
| Well A | 361 | 0.32 |
| Well A | 369 | 0.33 |
| Well C | 373 | 0.37 |
| Well B | 376 | 0.41 |
| Well A | 391 | 0.6 |
| Well B | 393 | 0.62 |
| Well D | 394 | 0.59 |
| Well A | 402 | 0.95 |
| Well D | 406 | 0.75 |
| Well B | 422 | 1.273 |
| Well D | 424 | 1.17 |
| Well D | 428 | 1.28 |
| Well C | 434 | 1.33 |
| Well A | 447 | 1.62 |
| Well D | 450 | 1.37 |
| Well A | 454 | 1.64 |

| | Most probable values of | |
|---|---|---|
| | Asphaltene diameter | Reference optical density |
| Top Model | | |
| Fit 1 | 2.06 | 0.27 |
| Fit 2 | 3.93 | 0.06 |
| Fit 3 | 2.06 | 0.83 |

TABLE 2-continued

| Second Model | | |
|---|---|---|
| Fit 1 | 2.26 | 0.27 |
| Fit 2 | 3.84 | 0.07 |
| Fit 3 | 2.26 | 0.68 |
| Third Model | | |
| Fit 1 | 2.06 | 0.27 |
| Fit 3 | 3.82 | 0.07 |
| Fit 3 | 2.06 | 0.83 |

The top models had similar fitted FHZ curves and varied in the number of outliers detected. The top models infer an FHZ fit inconsistent with asphaltene equilibrium, d~3.85 nm, (thin line) that resembles the lower portion of the FHZ EOS with diffusion model fit in FIG. 4 (curve 401). Also, the top models inferred an FHZ fit consistent with asphaltene equilibrium d~2.0 nm (left most heavy black line) that resembles the upper portion of the FHZ gravity only fit in FIG. 4 (curve 402). The last curve identified in all three model's flags measured optical densities that are inconsistent with the other two FHZ fits.

Figure 6:
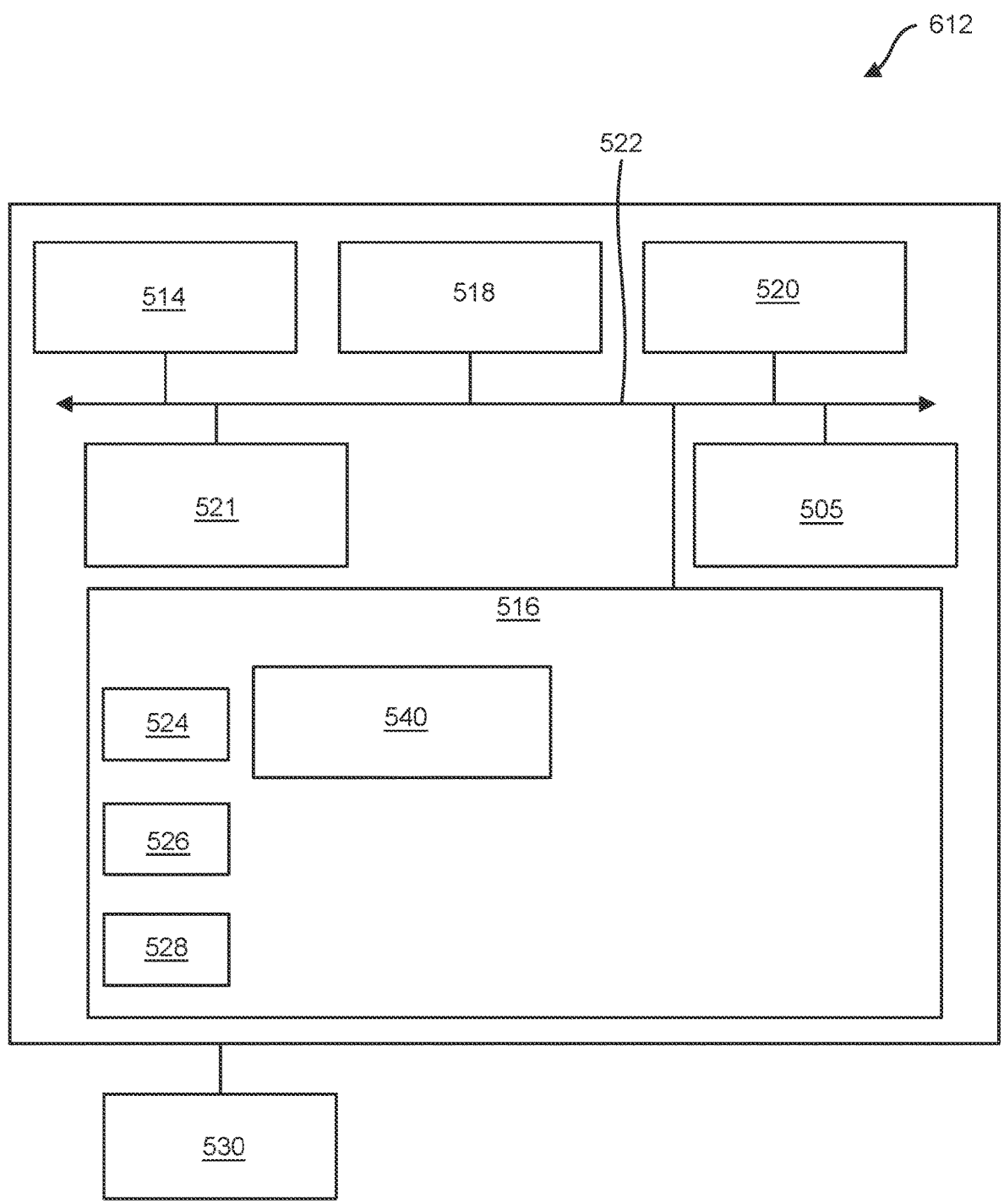
FIG. 6 depicts a schematic of an illustrative computing system for performing time synchronization between driller depth data as a function of time and downhole tool acceleration data as a function of time, according to one or more embodiments.

FIG. 6 depicts a schematic of an illustrative computing system 612 for performing time synchronization between driller depth data as a function of time and downhole tool acceleration data as a function of time, according to one or more embodiments. One or more chips, for example chips 505 and/or 521, can be or can include field-programmable gate arrays ("FPGAs"), application specific integrated circuits ("ASICs"), chiplets, Multi-Chip-Modules, central processing units ("CPUs"), and/or system-on-chips ("SOCs"), to name a few. The chip can be used in a wide-range of applications, including but not limited to auto emission control, environmental monitoring, digital voice recorders, or other digital processing systems. ASICs can include entire microprocessors, memory blocks including read only memory (ROM), random access memory (RAM), erasable programmable read only memory (EPROM), electrically erasable programmable read only memory (EEPROM), flash memory and other building blocks and can be known as system-on-chip ("SoC").

To achieve its desired functionality, the computing system 612 can include various hardware and software components. Among these components can be one or more processors 514 and an RFG Profiler 540. These hardware components can be interconnected through the use of a number of electrical connections, busses, and/or network connections. In one embodiment, the processor 514, the chip 505, the chip 521, and the RFG Profiler 540 can be communicatively coupled via a bus 522. The bus 522 can be or include any know computing system bus. The RFG Profiler 540 can be internal to a data storage device 516.

The chip 505, the chip 521, and/or the RFG Profiler 540 can include, either separately or in some combination, the necessary software and hardware, including tangible, non-transitory computer readable medium (not shown), for performing time synchronization between well logs. The RFG Profiler 540 can be integrated into or be the chip 505, the chip 521, and/or the processor 514, or can be software. The chip 505 and/or the chip 521 can be integrated into the processor 514. Although RFG Profiler 540 is depicted as being internal to the data storage device 516, in other examples, the controller module 534 can be a peripheral device (not shown) coupled to the computing system 612 or included within a peripheral device (not shown) coupled to the computing system 612. In other examples, the RFG Profiler 540 can be a peripheral device (not shown) coupled to the computing system 612 or included within a peripheral device (not shown) coupled to the computing system 612.

The RFG Profiler 540 can include instructions that when executed by the RFG Profiler 540 can cause the RFG Profiler 540 to perform time synchronization between two or more well logs. Referring to FIG. 1, the instructions can, when executed by the RFG Profiler 540, cause the RFG Profiler 540 to implement at least the functionality of utilizing domain knowledge, geological knowledge including zone information, and/or likelihood of presence of different asphaltene types as inputs to the processor 514 or the RFG Profiler 540, action 110 and utilizing downhole fluid analysis (DFA) measurements as inputs to the processor 514 or the RFG Profiler 540, action 120. Select an asphaltene diameter distribution based on downhole geographic region knowledge, the geological knowledge including zone information, and/or the likelihood of presence of different asphaltene types, action 130. The instructions can further include performing a model search by generating one or more models of the one or more downhole fluid analysis measurement data points by utilizing the asphaltene diameter distribution to fit a set of one or more equation of state curves to the one or more downhole fluid analysis measurement data points to define a model and compute the corresponding posterior distribution of asphaltene diameters, action 140. In other embodiments, the instructions can further include performing a model search by generating two or more models of the one or more downhole fluid analysis measurement data points by utilizing the asphaltene diameter distribution to fit a first set of one or more equation of state curves to the one or more downhole fluid analysis measurement data points and related measurement uncertainties to define a first model and generate one or more posterior distributions of asphaltene diameters and utilizing the asphaltene diameter distribution to fit a second set of one or more equation of state curves to the one or more downhole fluid analysis measurement data points and related measurement uncertainties to define a second model and generate one or more posterior distributions of asphaltene diameters, action 140. The instructions can further include ranking the plurality of models to create a top model action 150. In other embodiments, the instructions can further include ranking the plurality of models by fitted equation of state curves to the one or more downhole fluid analysis measurement data points and related measurement uncertainties to create a top model and determine from the top model one or more inferred distributions of fluid properties for the plurality of downhole geographic locations, action 150. The instructions can further include determining if the plurality of downhole geographic locations is in asphaltene equilibrium by determining whether the posterior distributions of the asphaltene diameters is consistent with that of asphaltenes in equilibrium, action 160. In other embodiments, the instructions can further include determining if the plurality of downhole geographic locations are in an asphaltene equilibrium by determining whether the one or more inferred distributions of fluid properties are that expected of fluid properties for a particular hydrocarbon type, action 160. The instructions can, when executed by the RFG Profiler 540, cause the RFG Profiler 540 to output a graphical representation of the analysis, curve fits, and related data. Returning to FIG. 6, in examples the RFG Profiler 540 can work in conjunction with the processor 514 to implement the functionality described above. In examples, the RFG Profiler 540 can execute firmware code stored on the computing system 612, such as on the chip 505, the chip 521, and/or the processor 514. The functionality of the computing system 612 and/or the RFG Profiler 540 can be in accordance with the processes of the present specification described herein. In the course of executing code, the processor 514 and/or the RFG Profiler 540 can receive input from and provide output to a number of the remaining hardware units.

The computing system 612 can be implemented in an electronic device. Examples of electronic devices include servers, desktop computers, laptop computers, cloud based computers, personal digital assistants ("PDAs"), mobile devices, smartphones, gaming systems, and tablets, among other electronic devices. The computing system 612 can be utilized in any data processing scenario including, standalone hardware, mobile applications, through a computing network, or combinations thereof. Further, the computing system 612 can be used in a computing network, a public cloud network, a private cloud network, a hybrid cloud network, other forms of networks, or combinations thereof. In one example, the processes provided by the computing system 612 are provided as a service by a third party.

To achieve its desired functionality, the computing system 612 can include various other hardware components. Among these other hardware components can be a number of data storage devices or tangible, non-transitory computer readable medium 516, a number of peripheral device adapters 518, and a number of network adapters 520. These hardware components can be interconnected through the use of a number of electrical connections, busses, and/or network connections. In one example, the processor 514, data storage device 516, peripheral device adapters 518, and a network adapter 520 can be communicatively coupled via a bus, for example the bus 522 as depicted in FIG. 5 or via a separate bus, not shown.

The chip 505, the chip 521, and/or the processor 514 can include the hardware and/or firmware/software architecture to retrieve executable code from the data storage device 516 and execute the executable code. The executable code can, when executed by the chip 505, the chip 521, and/or the processor 514, cause the chip 505, the chip 521, and/or the processor 514 to implement at least the functionality of utilizing domain knowledge, geological knowledge including zone information, and/or likelihood of presence of different asphaltene types as inputs to the processor 514 or the RFG Profiler 540, action 110 and utilizing downhole fluid analysis (DFA) measurements as inputs to the processor 514 or the RFG Profiler 540, action 120; selecting an asphaltene diameter distribution based on the domain knowledge, the geological knowledge including zone information, and/or the likelihood of presence of different asphaltene types, action 130; performing a model search by generating one or more models of the one or more downhole fluid analysis measurement data points by utilizing the asphaltene diameter distribution to fit a set of one or more equation of state curves to the one or more downhole fluid analysis measurement data points to define a model and compute one or more posterior distributions of asphaltene diameters action 140; ranking the plurality of models to create a top model or, action 150; determining if the plurality of downhole geographic locations are in an asphaltene equilibrium by determining whether the one or more of the posterior distributions of asphaltene diameters is consistent with asphaltenes in equilibrium, action 160.

In other embodiments, the executable code can cause the chip 505, the chip 521, and/or the processor 514 to implement at least the functionality of performing a model search by generating two or more models of the one or more downhole fluid analysis measurement data points by utilizing the asphaltene diameter distribution to fit a first set of one or more equation of state curves to the one or more downhole fluid analysis measurement data points and related uncertainties to define a first model and generate one or more posterior distributions of asphaltene diameter and utilizing the asphaltene diameter distribution to fit a second set of one or more equation of state curves to the one or more downhole fluid analysis measurement data points and related measurement uncertainties to define a second model and generate one or more posterior distributions of asphaltene diameters, action 140; ranking the plurality of models by fitted equation of state curves to the one or more downhole fluid analysis measurement data points and related measurement uncertainties to create a top model and determine from the top model one or more inferred distributions of fluid properties for the plurality of downhole geographic locations, action 150; determining if the plurality of downhole geographic locations are in an asphaltene equilibrium by determining whether the one or more inferred distributions of fluid properties are that expected of fluid properties for a particular hydrocarbon type, action 160.

The data storage device 516 can store data such as executable program code that is executed by the processor 514, the RFG Profiler 540, or other processing devices. The processor 514 can be a central processing unit that is to execute an operating system in the computing system 612. As will be discussed, the data storage device 516 can specifically store computer code representing a number of applications that the processor 514 and/or the RFG Profiler 540 can execute to implement at least the functionality described herein.

The data storage device 516 can include various types of memory modules, including volatile and nonvolatile memory. For example, the data storage device 516 of the present example can include Random Access Memory ("RAM") 524, Read Only Memory ("ROM") 526, and Hard Disk Drive ("HDD") storage 528. Many other types of memory can also be utilized, and the present specification contemplates the use of many varying type(s) of memory in the data storage device 516 as can suit a particular application of the principles described herein. In certain examples, different types of memory in the data storage device 516 can be used for different data storage needs. For example, in certain examples the processor 514 can boot from Read Only Memory ("ROM") 526, maintain nonvolatile storage in the Hard Disk Drive ("HDD") memory 528, and execute program code stored in Random Access Memory ("RAM") 524. In examples, the chip 505, and the chip 521 can boot from the Read Only Memory ("ROM") 526.

The data storage device 516 can include a computer readable medium, a computer readable storage medium, or a non-transitory computer readable medium, among others. For example, the data storage device 516 can be, an electronic, magnetic, optical, electromagnetic, infrared, or semiconductor system, apparatus, or device, or any suitable combination of the foregoing. More specific examples of the computer readable storage medium can include, for example, the following: an electrical connection having a number of wires, a portable computer diskette, a hard disk, a RAM, a ROM, an EPROM, a Flash memory, a portable compact disc read-only memory ("CD-ROM"), an optical storage device, a magnetic storage device, or any suitable combination of the foregoing. In the context of this document, a computer readable storage medium can be any tangible medium that can contain, or store computer usable program code for use by or in connection with an instruction execution system, apparatus, or device. In another example, a computer readable storage medium can be any non-transitory medium that can contain or store a program for use by or in connection with an instruction execution system, apparatus, or device.

The hardware adapters 518, 520 in the computing system 612 can enable the processor 514 to interface with various other hardware elements, external and internal to the computing system 612. For example, the peripheral device adapters 518 can provide an interface to input/output devices, such as, for example, a display device 530, a mouse, and/or a keyboard. The peripheral device adapters 518 can also provide access to other external devices such as an external storage device, a number of network devices such as, for example, servers, switches, and routers, client devices, other types of computing devices, and combinations thereof.

The display device 530 can be provided to allow a user of the computing system 612 to interact with and implement the functionality of the computing system 612. Examples of display devices 530 can include a computer screen, a laptop screen, a mobile device screen, a personal digital assistant ("PDA") screen, and/or a tablet screen, among other display devices 530.

The peripheral device adapters 518 can also create an interface between the processor 514 and the display device 530, a printer, or other media output devices. The network adapter 520 can provide an interface to other computing devices within, for example, a network, thereby enabling the transmission of data between the computing system 612 and other devices located within the network. The network adapter 520 can provide an interface to an external telecommunications network such as a cellular phone network or other radio frequency enabled network, thereby enabling the transmission of data between the computing system 612 and other external devices such as an external storage device, a number of network devices such as, for example, servers, switches, and routers, client servers, radio frequency enabled devices, other client devices, other types of computing devices, and combinations thereof.

The computing system 612 can further includes a number of modules used in the implementation of the systems and processes described herein. The various modules within the computing system 612 can include executable program code that can be executed separately. In this example, the various modules can be stored as separate computer program products. In another example, the various modules within the computing system 612 can be combined within a number of computer program products; each computer program product including a number of the modules.

Figure 7:
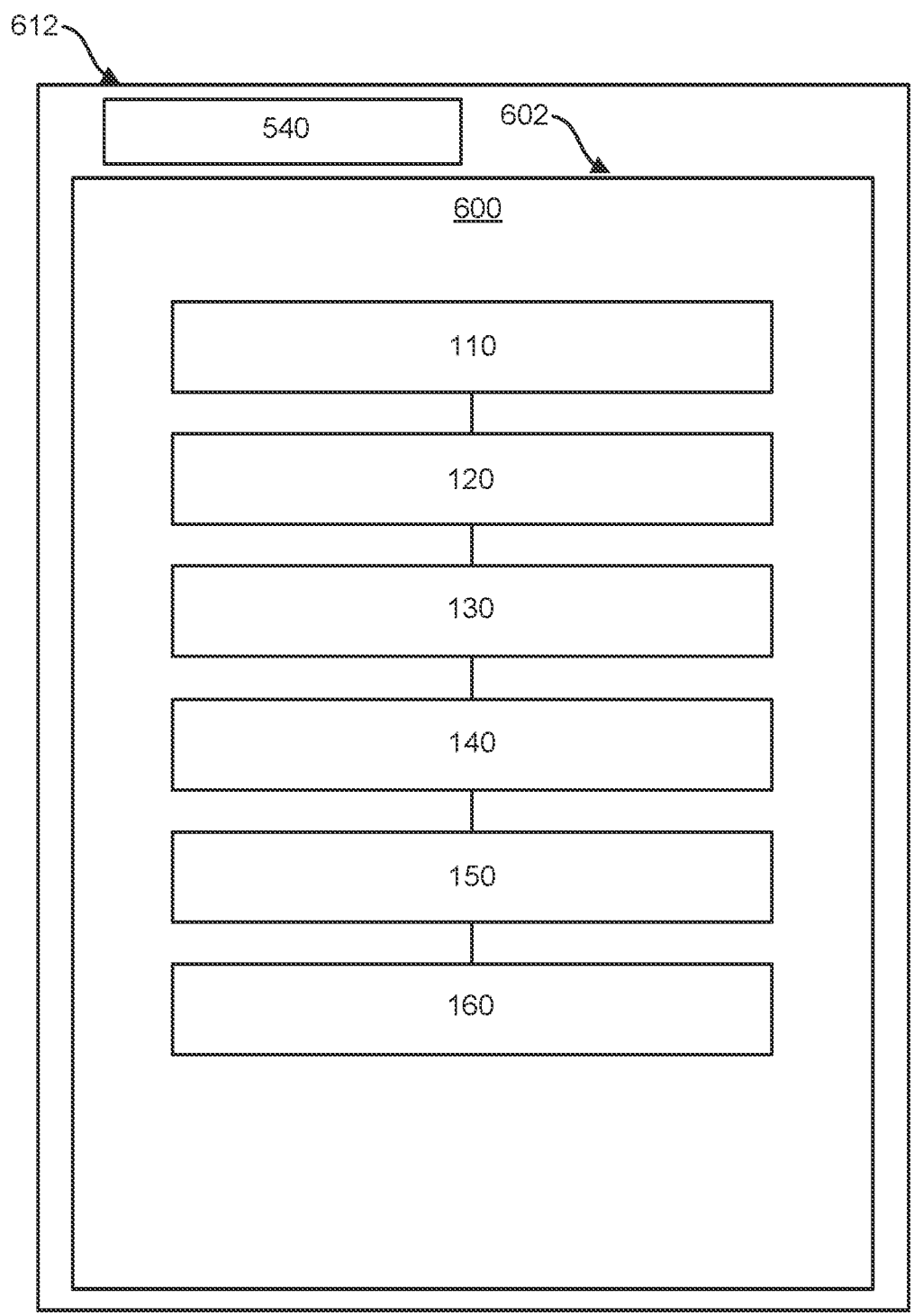
FIG. 7 depicts an illustrative computing device including the RFG Profiler and a non-transitory computer-readable medium including computer executable instructions stored thereon within the computing system of FIG. 6, according to one or more embodiments.

FIG. 7 depicts an illustrative computing device including the RFG Profiler 540 and a non-transitory computer-readable medium 602 including computer executable instructions 600 stored thereon within the computing system of FIG. 6, according to one or more embodiments. When the computer executable instructions 600 are executed by the RFG Profiler 540, the computer executable instructions 600 can cause the RFG Profiler 540 to implement at least the functionality of utilizing domain knowledge, geological knowledge including zone information, and/or likelihood of presence of different asphaltene types as inputs to the processor 514 or the RFG Profiler 540, block 110 and utilizing downhole fluid analysis (DFA) measurements as inputs to the processor 514 or the RFG Profiler 540, block 120; selecting an asphaltene diameter distribution based on the domain knowledge, the geological knowledge including zone information, and/or the likelihood of presence of different asphaltene types, block 130; performing a model search by generating one or more models of the one or more downhole fluid analysis measurement data points by utilizing the asphaltene diameter distribution to fit a set of one or more equation of state curves to the one or more downhole fluid analysis measurement data points to define a model of and compute one or more posterior distributions of asphaltene diameters, block 140; ranking the plurality of models to create a top model, block 150; determining if the plurality of downhole geographic locations are in an asphaltene equilibrium by determining whether the posterior distributions of the asphaltene diameters are consistent with that of asphaltenes in equilibrium, block 160.

In other embodiments, the computer executable instructions 600 can cause the RFG Profiler 540 to implement at least the functionality of performing a model search by generating two or more models of the one or more downhole fluid analysis measurement data points by utilizing the asphaltene diameter distribution to fit a first set of one or more equation of state curves to the one or more downhole fluid analysis measurement data points and related measurement uncertainties to define a first model and generate one or more posterior distributions of asphaltene diameters and utilizing the asphaltene diameter distribution to fit a second set of one or more equation of state curves to the one or more downhole fluid analysis measurement data points and related measurement uncertainties to define a second model and generate one or more posterior distributions of asphaltene diameters, block 140; ranking the plurality of models by the fitted equation of state curves to the one or more downhole fluid analysis measurement data points and related measurement uncertainties to create a top model and determine from the top model one or more inferred distributions of fluid properties for the plurality of downhole geographic locations, block 150; determining if the plurality of downhole geographic locations are in an asphaltene equilibrium by determining whether the one or more inferred distributions of fluid properties are that expected of fluid properties for a particular hydrocarbon type, block 160. The computer executable instructions 600 can cause the RFG Profiler 540 to output a graphical representation of the analysis, curve fits, and related data.

The present disclosure further relates to any one or more of the following numbered paragraphs:

1. A process for determining asphaltene equilibrium between two or more downhole geographic locations comprising: measuring one or more fluid properties of a plurality of fluid samples at varying downhole depths to generate a one or more downhole fluid analysis measurement data points; selecting an asphaltene diameter distribution based on prior knowledge; utilizing the asphaltene diameter distribution to fit a first set of one or more equation of state curves to the one or more downhole fluid analysis measurement data points to define a first model of fitted equation of state curves and to determine one or more posterior distributions of asphaltene diameters; and determining if the varying downhole depths are in an asphaltene equilibrium by determining whether the one or more posterior distributions of asphaltene diameters is consistent with that of asphaltenes in equilibrium.

2. The process of paragraph 1, wherein the one or more fluid properties is an optical density, a fluid density, a fluid composition, or a combination thereof.

3. The process of paragraph 1 or 2, wherein the equation of state comprises a Flory-Huggins-Zuo equation of state or a modification thereof.

4. The process according to any of paragraphs 1 to 3, where a plurality of models of fitted equation of state curves is obtained by fitting a plurality of sets of one or more equations of state curves and determine model dependent posterior distributions of asphaltene diameters.

5. The process according to any of paragraphs 1 to 4, wherein each model in the plurality of models is ranked; and wherein the ranking of the models guides a placement of a downhole measurement location to discriminate against competing models.

6. The process according to any of paragraphs 1 to 5, wherein a plurality of models differing in the number of asphaltene gradients is ranked based on predictive performance and/or physical interpretability.

7. The process according to any of paragraphs 1 to 6, further comprising: outputting the top model onto a graphical display and visually assessing the data fits on the one or more equation of state curves to determine if the plurality of varying downhole depths belong to the same flow unit.

8. The process according to any of paragraphs 1 to 7, further comprising selecting one or more downhole locations for additional downhole fluid sampling based on the asphaltene equilibrium determination to update the model.

9. The process according to any of paragraphs 1 to 8, wherein an asphaltene disequilibrium or an asphaltene quasi-equilibrium is determined.

10. The process according to any of paragraphs 1 to 9, further comprising: performing a three-dimensional geometric assessment of a downhole condition to assess downhole fluid geodynamics processes.

11. The process according to any of paragraphs 1 to 10, wherein uncertainties in the one or more measured fluid properties are captured within a likelihood function comprising an equation of state and measurement error.

12. The process according to any of paragraphs 1 to 11, wherein the uncertainties in the one or more measured fluid properties include both inherent stochasticity as well as uncertainty in the measurement.

13. The process according to any of paragraphs 1 to 12, further comprising: including an estimate of uncertainty in measurement data; and accounting for different possible sources of error selected from the group consisting of: depth, tool, and contamination.

14. The process according to any of paragraphs 1 to 13, wherein an uncertainty in the asphaltene diameter is captured in a prior distribution honoring the Yen-Mullins model for asphaltene content.

15. A process for determining asphaltene equilibrium between two or more downhole geographic locations comprising: measuring one or more fluid properties of a plurality of fluid samples at varying downhole depths to generate a plurality of fluid property measurements; correlating the plurality of fluid property measurements and any associated fluid sample measurement uncertainties for each measurement to the downhole depth at which each fluid property was measured to define a one or more downhole fluid analysis measurement data points and related measurement uncertainties associated with a plurality of downhole geographic locations; selecting an asphaltene diameter distribution based on prior knowledge of a downhole geographic region; utilizing the asphaltene diameter distribution to fit a first set of one or more equation of state curves to the one or more downhole fluid analysis measurement data points and related measurement uncertainties to define a first model and generate one or more posterior distributions of asphaltene diameters and utilizing the asphaltene diameter distribution to fit a second set of one or more equation of state curves to the one or more downhole fluid analysis measurement data points and related measurement uncertainties to define a second model and generate one or more posterior distributions of asphaltene diameters; ranking the first and second models by fitted equation of state curves to the one or more downhole fluid analysis measurement data points and related measurement uncertainties to create a top model; determining from the top model one or more inferred distributions of fluid properties for the plurality of downhole geographic locations; and determining if the plurality of downhole geographic locations is in an asphaltene equilibrium by determining whether the one or more inferred distributions of fluid properties are that expected of fluid properties for a particular hydrocarbon type.

16. The process of paragraph 15, wherein the plurality of fluid samples is at least one fluid sample.

17. The process of paragraph 15 or 16, wherein the one or more fluid properties is an optical density, a pressure, an asphaltene concentration, a temperature, a fluid density, a fluid viscosity, a retrograde dew formation, an asphaltene precipitation, a gas evolution, or a combination thereof.

18. The process according to any of paragraphs 15 to 17, wherein the first and second equations of state comprise a Flory-Huggins-Zuo equation of state, a modified FHZ EOS that accounts for diffusion, a van der Waals EOS, a Redlich-Kwong EOS, a Soave Redlich-Kwong EOS, a Peng-Robinson EOS, a Stryjek-Vera-Peng-Robinson EOS, a Patel-Teja EOS, or a SAFT-type EOS.

19. The process according to any of paragraphs 15 to 18, wherein the first and second set of equations of state are the same or different equations of state.

20. The process according to any of paragraphs 15 to 19, further comprising: outputting the top model onto a graphical display and visually assessing the data fits on the one or more equation of state curves to determine if the plurality of downhole geographic locations belong to the same flow unit.

21. The process according to any of paragraphs 15 to 20, further comprising: utilizing the asphaltene diameter distribution and a third equation of state to fit a third set of one or more equation of state curves to the plurality of fluid analysis measurement data points and related measurement uncertainties to define a third model of fitted equation of state curves; and ranking the first, second, and third models of fitted equation of state curves by best fitted curves to the plurality of fluid analysis measurement data points and related measurement uncertainties to create the top model.

22. The process according to any of paragraphs 15 to 21, further comprising selecting one or more downhole locations for additional downhole fluid sampling based on the asphaltene equilibrium determination.

23. The process according to any of paragraphs 15 to 22, further comprising: performing a three-dimensional geometric assessment of a downhole condition to assess downhole fluid geodynamics processes.

24. The process according to any of paragraphs 15 to 23, wherein the particular hydrocarbon type comprises a light oil, a black oil, or a heavy oil.

25. A process for determining asphaltene equilibrium in a reservoir that combines geological knowledge and domain expert knowledge with downhole fluid analysis measurements, the process comprising: selecting one of a plurality of depth zones of interest based on geological information, pressure data, logs, and/or seismic data; choosing a prior distribution on an asphaltene diameter; and solving an equation of state.

26. The process of paragraph 25, further comprising: fitting a known number of distinct asphaltene gradients to the equation of state.

27. The process of paragraph 25 or 26, wherein uncertainty in a measured optical density is captured within a likelihood function relating the equation of state and a measurement error.

28. The process according to any of paragraphs 25 to 27, further comprising: including a function that estimates uncertainty in measurement data, accounting for different possible sources of error selected from the group consisting of: depth, tool, and contamination.

29. The process according to any of paragraphs 25 to 28, wherein uncertainty in the asphaltene diameter is captured in a prior distribution honoring the Yen-Mullins model for asphaltene content.

30. The process according to any of paragraphs 25 to 29, wherein a plurality of models differing in the number of asphaltene gradients are ranked based on predictive performance and/or physical interpretability.

31. The process according to any of paragraphs 25 to 30, wherein the ranking of potential models guides a placement of a new downhole geographic location for additional measurements that can used to discriminate against competing models.

32. The process according to any of paragraphs 25 to 31, wherein the equation of state comprises a Flory-Huggins-Zuo equation of state model.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A process for determining asphaltene equilibrium between two or more downhole geographic locations comprising:
    measuring one or more fluid properties of a plurality of fluid samples at varying downhole depths to generate a one or more downhole fluid analysis measurement data points;
    selecting an asphaltene diameter distribution based on prior knowledge;
    utilizing the asphaltene diameter distribution to fit a set of one or more equation of state curves to the one or more downhole fluid analysis measurement data points to define a model of fitted equation of state curves and to determine one or more posterior distributions of asphaltene diameters, wherein a plurality of models of fitted equation of state curves is obtained by fitting a plurality of sets of one or more equations of state curves and determine model dependent posterior distributions of asphaltene diameters; and
    determining if the varying downhole depths are in an asphaltene equilibrium by determining whether the one or more posterior distributions of asphaltene diameters is consistent with that of asphaltenes in equilibrium.

2. The process of claim 1, wherein the one or more fluid properties is an optical density, a fluid density, a fluid composition, or a combination thereof.

3. The process of claim 1, wherein the equation of state comprises a Flory-Huggins-Zuo equation of state or a modification thereof.

4. The process of claim 1, wherein each model in the plurality of models is ranked; and wherein the ranking of the models guides a placement of a downhole measurement location to discriminate against competing models.

5. The process of claim 4, further comprising: outputting the top model onto a graphical display and visually assessing the data fits on the one or more equation of state curves to determine if the plurality of varying downhole depths belong to the same flow unit.

6. The process of claim 4, wherein the one or more fluid properties is an optical density, a fluid density, a fluid composition, or a combination thereof.

7. The process of claim 4, wherein the equation of state comprises a Flory-Huggins-Zuo equation of state or a modification thereof.

8. The process of claim 4, wherein a plurality of models differing in number of asphaltene gradients is ranked based on predictive performance and/or physical interpretability.

9. The process of claim 4, further comprising:
    performing a three-dimensional geometric assessment of a downhole condition to assess downhole fluid geodynamics processes.

10. The process of claim 5, wherein the one or more fluid properties is an optical density, a fluid density, a fluid composition, or a combination thereof.

11. The process of claim 5, wherein the equation of state comprises a Flory-Huggins-Zuo equation of state or a modification thereof.

12. The process of claim 5, wherein a plurality of models differing in number of asphaltene gradients is ranked based on predictive performance and/or physical interpretability.

13. The process of claim 1, wherein a plurality of models differing in number of asphaltene gradients is ranked based on predictive performance and/or physical interpretability.

14. The process of claim 1, further comprising selecting one or more downhole locations for additional downhole fluid sampling based on the asphaltene equilibrium determination to update the model.

15. The process of claim 1, wherein an asphaltene disequilibrium or an asphaltene quasi-equilibrium is determined.

16. The process of claim 1, further comprising:
performing a three-dimensional geometric assessment of a downhole condition to assess downhole fluid geodynamics processes.

17. The process of claim 1, wherein uncertainties in the one or more measured fluid properties are captured within a likelihood function comprising an equation of state and measurement error.

18. The process of claim 17, wherein the uncertainties in the one or more measured fluid properties include both inherent stochasticity as well as uncertainty in the measurement.

19. The process of claim 17, further comprising: including an estimate of uncertainty in measurement data; and accounting for different possible sources of error selected from the group consisting of: depth, tool, and contamination.

20. The process of claim 17, wherein an uncertainty in the asphaltene diameter is captured in a prior distribution honoring the Yen-Mullins model for asphaltene content.

* * * * *